United States Patent

Le Lem et al.

[11] Patent Number: 5,851,511
[45] Date of Patent: Dec. 22, 1998

[54] POLYIODO COMPOUNDS, THEIR PREPARATION AND THEIR USE IN X-RAY RADIOLOGY

[75] Inventors: Gaël Le Lem, Saint-Cloud; Dominique Meyer, Saint-Maur, both of France

[73] Assignee: Guerbet S.A., Villepinte, France

[21] Appl. No.: 809,758

[22] PCT Filed: Sep. 20, 1995

[86] PCT No.: PCT/FR95/01212

§ 371 Date: Mar. 21, 1997

§ 102(e) Date: Mar. 21, 1997

[87] PCT Pub. No.: WO96/09280

PCT Pub. Date: Mar. 28, 1996

[30] Foreign Application Priority Data

Sep. 22, 1994 [FR] France ................... 94 11329

[51] Int. Cl.[6] .............. A61K 49/04; C07C 233/65
[52] U.S. Cl. .............. 424/9.452; 564/153; 514/616
[58] Field of Search ............. 564/153; 424/9.452; 514/616

[56] References Cited

U.S. PATENT DOCUMENTS

| | | | |
|---|---|---|---|
| 4,065,553 | 12/1977 | Tilly et al. | 424/5 |
| 4,065,554 | 12/1977 | Tilly et al. | 424/5 |
| 4,283,381 | 8/1981 | Speck et al. | 424/9.454 |
| 5,709,846 | 1/1998 | [Le]Lem et al. | 424/9.452 |

FOREIGN PATENT DOCUMENTS

| | | |
|---|---|---|
| 0501875 | 6/1994 | European Pat. Off. |
| 92 18167 | 10/1992 | WIPO |
| 93 10824 | 6/1993 | WIPO |
| 94 21600 | 9/1994 | WIPO |
| 95 01966 | 1/1995 | WIPO |

*Primary Examiner*—Gary E. Hollinden
*Attorney, Agent, or Firm*—Jacobson, Price, Holman & Stern, PLLC

[57] ABSTRACT

The invention relates to compounds of formula:

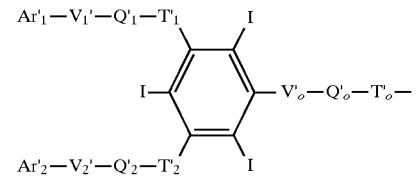

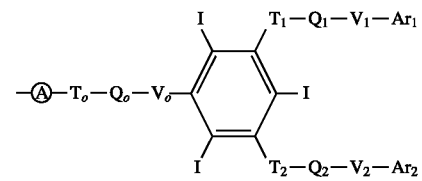

in which
$T_i$, $V_i$, $T'_i$ and $V'_i$ with i=0, 1 or 2, represent O, COND or NDCO, D being H, alkyl or (poly)hydroxyalkyl;
$Q_i$ and $Q'_i$ with i=0, 1 or 2, represent alkylene or (poly)hydroxyalkylene;
$Ar_i$ and $Ar'_i$ with i=1 or 2, represent

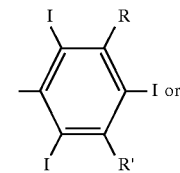

in which R, $R_3$, $R_4$ are COOH and R', $R'_3$, $R'_4$ are $CONR'_1R'_2$ or $N(R'_1)COR'_2$, R' and $R'_2$ being H, alkyl or (poly)hydroxyalkyl such that $R'_1$ and $R'_2$ together comprise at least 4 hydroxyl groups,
or $R_i$ and $R'_i$ with i=nothing, 3 or 4 represent $CONR'_1R'_2$ or $N(R'_1)COR'_2$, $R'_1$ and $R'_2$ together comprising at least 6 hydroxyl groups,
or else $R_i$ and $R'_i$ with i=3 or 4 represent T—Q—V—Ar, T, Q and V being as defined above for $T_i$, $Q_i$ and $V_i$ and Ar having formula II,
and A is a biocompatible radical of molecular weight less than 1200 having two valences such as to give with $T_o$ and $T'_o$ an amide or ether group.

24 Claims, No Drawings

POLYIODO COMPOUNDS, THEIR PREPARATION AND THEIR USE IN X-RAY RADIOLOGY

The present invention relates to compounds which can be used as contrast agents for X-ray radiology.

These compounds, which comprise at least 6 phenyl rings bearing 3 or 4 iodine atoms, give aqueous solutions whose concentration of iodine atoms is of the order of those generally used clinically, from 5 to 40 g of iodine per 100 ml, and which have a viscosity which is acceptable for parenteral administration, despite a molecular weight of more than 3,000. They are, moreover, eliminated from the blood circulation, after intravascular administration, markedly more slowly than the known compounds, with the exclusion of polymers on which iodo molecules are grafted as described in EP-A-354,836 and WO 93/10824, but whose clinical use is still not established, in particular due to the polydispersity of their molecular weights.

Thus, after intravenous injection into an animal of the same dose, expressed as weight of iodine, of a monomer of the invention or of a contrast agent commonly used clinically—such as iobitridol or iohexol—it is observed that the concentration of iodine in the blood decreases much less quickly for the compounds of the invention in the first minutes following the administration. For example, in rats, after 5 minutes, the concentration for a compound according to the invention is generally at least 3 times higher. Since, moreover, the presence of hydrophilic groups which are properly distributed on the molecule affords these compounds good water solubility, greater than 25 g of iodine per liter, they are useful as contrast agents for X-ray imaging of the vascular compartment.

The compounds of the invention have formula I:

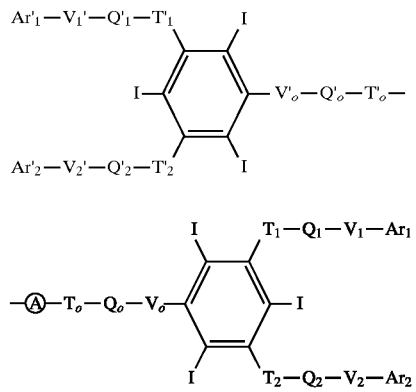

in which:

$T_i$, $V_i$, $T'_i$ and $V'_i$, which are identical or different, with i=0, 1 or 2, are selected from the group consisting of O, CO—ND and ND—CO, and D is selected from the group consisting of H, $C_1$ to $C_6$ alkyl and $C_1$ to $C_6$, preferably $C_1$ to $C_4$, hydroxyalkyl or polyhydroxyalkyl;

$Q_i$ and $Q'_i$, which are identical or different, with i=0, 1 or 2, are selected from the group consisting of $C_1$ to $C_6$ alkylene and $C_1$–$C_6$, preferably $C_1$ or $C_2$, hydroxyalkylene or polyhydroxyalkylene;

$Ar_i$ and $Ar'_i$, which are identical or different, with i=1 or 2, are selected from the group consisting of:
either formula II

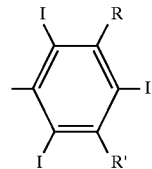

in which
R is COOH and R' is selected from the group consisting of $CONR'_1R'_2$ and $N(R'_1)COR'_2$, $R'_1$ and $R'_2$ being selected from the group consisting of H, $C_1$ to $C_4$ alkyl and $C_1$ to $C_8$ hydroxyalkyl or polyhydroxyalkyl and together comprising more than 4 hydroxyls and preferably more than 6 hydroxyls, or R and R', which are identical or different, are selected from the group consisting of $CONR'_1R'_2$ and $N(R'_1)COR'_2$, $R'_1$ and $R'_2$ being selected from the group consisting of H, $C_1$ to $C_4$ alkyl and $C_1$ to $C_8$ hydroxyalkyl or polyhydroxyalkyl and together comprising at least 6 hydroxyls and preferably more than 8 hydroxyls, and better at least 10 hydroxyls,
or formula III

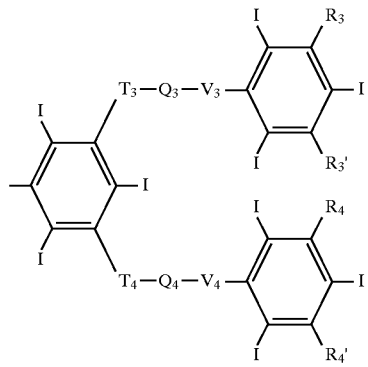

in which
the groups $T_i$, $Q_i$ and $V_i$ with i=3 or 4 have one of the meanings of the case i=0 and $R_i$ and $R'_i$ with i=3 or 4 have one of the meanings of R and R' in formula II or are T—Q—V—Ar with Ar being formula II and T, Q and V having the meanings of $T_i$, $Q_i$ and $V_i$, and A is a biocompatible radical from an aliphatic or aromatic molecule of molecular weight less than 1200, optionally comprising hetero atoms chosen from oxygen, nitrogen and iodine, having two free valences such as to give with $T_0$ and $T'_0$ an amide or ether group, as well as pharmaceutically acceptable salts with bases of these acids, such as alkali metal salts, salts of aliphatic amines such as N-methylglucamine or salts of amino acids such as lysine.

The alkyl groups may be linear or branched.

The structure of A is not critical insofar as, depending on the case, A can form with $T_0$ and $T'_0$ two amide and/or oxide ether groups.

Among the suitable aliphatic radicals A, mention may be made of derivatives
of diamines, such as $H_2N$—$(CH_2)_n$—$NH_2$ with n=2 to 4, the alkylene chain optionally being interrupted by an oxygen atom or an amide group and possibly substituted by one or more hydroxyls;

or of diacids, such as fumaric acid or succinic acid, or those of formula HOOC—$(CH_2)_n$—COOH in which n=1 to 4 or of dialcohols, such as ethylene glycol, or of an amino acid such as γ-aminobutyric acid.

Among the suitable aromatic radicals A, mention may be made of phenyl ring, substituted or unsubstituted, if appropriate by iodine, such that the radical $T'_0$—A—$T_0$ may be obtained from phenyldicarboxylic acids, phenylenediamines or aminophenylcarboxylic acids, optionally substituted by iodine, in particular tetraiodophthalic acid and isomers thereof, 3-acetylaminotriiodoisophthalic acid, diiodo-p-phenylenediamine and iodohydroxybenzoic acids.

Radicals comprising two phenyl rings are other examples of A, such as those derived from 4,4'-biphenyldicarboxylic acid or from bisphenol.

Compounds in which the two substituents of A groups are identical and more particularly those in which the substituents $T_i$—$Q_i$—$V_i$—$Ar_i$ are identical are preferred.

Given the use of the compounds as contrast agents, it is also desirable for them to comprise the maximum number of iodine atoms, and compounds in which A have iodine atoms on a phenyl ring are preferred.

The compounds for which $Ar_i$ and $Ar'_i$ have formula III, $R_i$ and $R'_i$ having the meaning of R and R', exhibit excellent vascular retention time and they are preferred.

The process for the preparation of the compounds of formula I is also provided in accordance with the invention.

These compounds may be prepared by reacting, in the first step, the radical A bearing the suitable reactive groups, with a molecule which constitutes part of the groups substituting it in formula I and, for example, with $T^\alpha_0$—$Q_0$—$V^\alpha_0$, or with

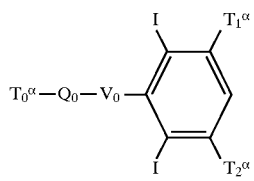

in which formulae the exponents α mean that the group is a functional group which is a precursor of the group of formula I and, for example, when $T_1$ is CONH, $T_1^\alpha$ is COOH or COCl and when $T_1$ is O, $T_1^\alpha$ is OH, halogen or sulphonate.

Another part of substituent groups is then reacted with the compound obtained to give, step by step, by standard amidation or etherification reactions, compound of formula I.

Nevertheless, it is preferred firstly to prepare substituent groups having formula

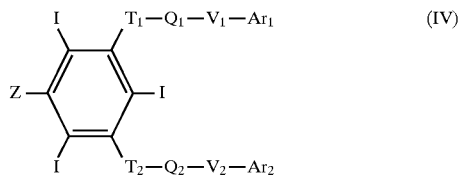

in which the groups $T_i$, $Q_i$, $V_i$ and $Ar_i$ have their meanings of formula I and Z represents either $T^\alpha_0$—$Q_0$—$V_0$, or $V^\alpha_0$, in which case, in the last step, a radical A will be reacted, on which $T_0$—$Q_0$—$V^\beta_0$ will have been grafted beforehand, $V^\beta_0$ being a functional group which, on reaction with $V^\alpha_0$, gives $V_0$.

The preparation of the compound of formula IV comprises:

1) reaction of the compound of formula

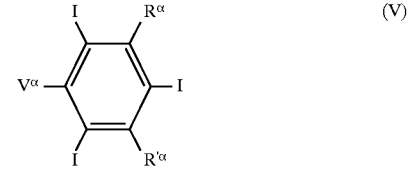

in which $R^\alpha$, $R'^\alpha$ and $V^\alpha$ represent COCl or $NH_2$ or alternatively $V^\alpha$ represents OH, depending on the nature of $R_i$, $R'_i$ and $V_i$ in formula IV, with, when the groups $R^\alpha$ represent COCl, an amino alcohol of formula $HNR'_1R'_2$ and when the groups $R^\alpha$ represent $NH_2$, with $R'_2COCl$ or $R'_2COOH$, it being possible for this reaction to be followed by alkylation of the amide obtained, for example with $R'_1Cl$;

2) reaction of the product obtained with $T^\alpha$—Q—$V^\beta$ $T^\alpha$ and $V^\beta$ being precursor groups of $T_i$ and $V_i$, it being possible for the order of reactions 1 and 2 to be reversed;

3) reaction of the product obtained with

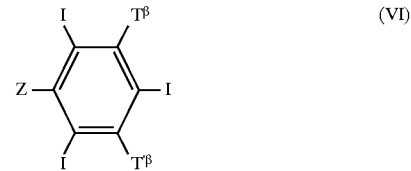

the exponent β denoting precursor groups of T, namely $T_1$ and $T_2$ when, in the compound of formula I, $Ar_i$ is formula II, or $T_3$ and $T_4$ when $Ar_i$ is formula III, and Z is either a precursor group $T^\beta_i$—$Q_i$—$V_i$ or a precursor group $V_i\beta$, in which case the compound obtained will have to react with $T^\beta_i$—$Q_i$—$V^\beta_i$ before the following step;

4) optionally, in the case where $Ar_i$ of formula I is formula III, a further reaction of T—Q—V—Ar thus obtained with a compound of formula VI in which $T^\beta$ and $T'^\beta$ denote the precursors of $T_1$ and $T_2$;

5) reaction of the group of formula IV with A substituted by a precursor group of $T_0$, optionally followed by salification of the carboxylic acid groups.

Given the structure of the groups R, T and V, the reactions carried out in the course of this process are conventional amidation or etherification reactions, bearing in mind that the reactivity of functional groups substituted on a phenyl ring is low when the two adjacent carbon atoms are substituted by an iodine atom.

Thus, amides are prepared by the action of an acid chloride on a suitable amine, in an aprotic solvent in which they are insoluble, preferably in the presence of a compound capable of binding the hydrochloric acid released, such as a tertiary amine, for example triethylamine or tributylamine; they may also be obtained by the action of the acid on the amine in solution, in the presence of a coupling agent, such as those used in peptide chemistry, for instance N,N'-dicyclohexylcarbodiimide, 1-(3-dimethylaminopropyl)-3-ethylcarbodiimide or 1-ethoxycarbonyl-2-ethoxy-1,2-dihydroquinoline, optionally in the presence of an activator, hydroxybenzotriazole or N-hydroxysuccinimide.

The amino groups which do not need to react are blocked, for example as phthalimide.

The ether groups are prepared by the action of a halide or a sulphonate on a suitable alcohol or phenol in the presence of a strong base, in a manner which is known per se.

In the course of these reactions, the alcohol functions may advantageously be protected as ester.

Among the starting triiodophenyl rings, mention may be made of 3,5-diamino-2,4,6-triiodobenzoic acid described in DE(East) 43,994 or GB 791,997 or 782,313 and 4-hydroxy-2,4,6-terephthalic acid described in Chem. Abs. 69 86643-6.

Their acid chlorides, prepared by the action of $SOCl_2$, are reacted either with a suitable amino alcohol, whose hydroxyls have optionally been protected by esterification, or with an amine to create the bridge between this ring and A or another phenyl ring; in a second step, the phenol or aniline functional groups are reacted under conventional conditions.

The amino alcohols $NHR'_1R'_2$ in which $R'_1$ and $R'_2$ each contain at least one hydroxyl and together contain at least 6 or better still, more than 8 hydroxyls are preferred.

Among the latter, mention may be made of those having
$R'_1=CH_2-(CHOH)_4-CH_2OH$ and $R'_2=CH_2-(CHOH)_4-CH_2OH$ or
$R'_2=CH_2-CH_2OH$ or $R'_2=CH_2-CHOH-CH_2OH$
which are commercially available, $$-R'_1=CH-(CHOH)_3-CH_2OH$$
$$\phantom{-R'_1=CH}|$$
$$\phantom{-R'_1=CH-}CH_2OH$$

and $R'_2=CH_2-CHOH-CH_2OH$ described in EP-A-558,395, $R'_1=R'_2=CH_2-(CHOH)_3-CH_2OH$ described in J. Org. Chem. 35(2) 464–7 (1970), $R'_1=R'_2=CH_2-(CHOH)_2-CH_2OH$ described in U.S. Pat. No. 4,661,646.

Other amino alcohols may be prepared by disubstitution of benzylamine with a halo or sulpho derivative of a suitable alcohol followed by debenzylation of the compound obtained, in particular by reaction with $H_2$; a hydroxylated aldehyde such as a saccharide may also be reacted with a primary amino alcohol and the imine obtained reduced by reaction with $H_2$.

Compounds having $$-R'_1=CH-CHOH-CH_2OH$$
$$\phantom{-R'_1=CH}|$$
$$\phantom{-R'_1=CH-}CH_2OH$$

$R'_2=CH_2-CHOH-CH_2OH$ or $R'_2=CH_2-(CHOH)_2-CH_2OH$ or
$-R'_1=CH_2-(CHOH)_3-CH_2OH$ $R'_2=CH_2-CHOH-CH_2OH$ or $R'_2=CH_2-(CHOH)_2-CH_2OH$ are thus obtained.

Radio-opaque contrast agent compositions which comprise as X-ray absorbing product at least one of the compounds of formula I are also provided according to the invention. These compositions may be administered orally, rectally or parenterally, in particular via the intravenous, intraarterial, intrabronchial or intraarachnoid route in a suitable pharmaceutical form.

Given their pharmacokinetics, they are particularly suitable for cardiac and vascular imaging.

The carriers may be those conventionally used in this field of radiological diagnostics, with which the known additives may be associated in order to adjust the osmolality or the pH or to decrease certain side effects known for highly iodinated products.

For intravenous administration, in particular for observation of vascular compartment, isoosmolar aqueous solutions, of pH about 7, which contain from 5 g to 40 g of iodine substituted on phenyl rings per 100 ml, from 10 ml to 250 ml of which will be administered, are preferred.

Examples of compounds of the invention and prior to this the preparation of molecules which will be bound to the core A are described hereinbelow.

A) Preparation of compound $C_1$ having formula VIII:

$T^\alpha-Q-V-$ [triiodophenyl ring with substituents I, R, I, R', I]

with $R=R'=CON-(CH_2(CHOH)_4CHOH)_2$  $T^\alpha-Q-V=H_2N-CH_2-CO-NH$

Reaction scheme:

[phthalimide]-$N-CH_2-CO-NH-$[triiodophenyl with COCl, I, COCl, I substituents]$ + HN(CH_2-(CHOH)_4-CH_2OH$

↓

Diamide + HCl

↓ $+NH_2-NH_2$

-continued

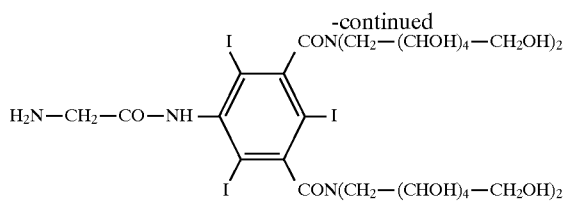

Step (a)

258 g of N-phthaloylglycine chloride are introduced slowly, with stirring, into a solution at 0° C. of 238 g of 5-amino-2,4,6-triiodoisophthalic acid dichloride in 1 liter of dimethylacetamide; the mixture is stirred for several hours at 0° C. and, after one night at room temperature, it is then introduced slowly into 20 liters of water; the precipitate formed is isolated and dissolved in 6 liters of ethyl acetate. This solution is washed with aqueous sodium bicarbonate solution and then with water, dried and then concentrated. 250 g of 2,4,6-triiodo-5-phthalimidoacetamidoisophthalic acid dichloride are obtained.

Step (b)

208 g of the above acid dichloride, 416 g of the commercial amine and 100 ml of triethylamine are dissolved in 2 liters of N-methylpyrrolidone or dimethylacetamide and the solution is maintained at 70° C. for 24 hours. The precipitate formed is separated out and the solvent is removed by distillation under reduced pressure. The residue, dissolved in the minimum amount of water at pH 3, is passed through a cation-exchange resin (1.5 l of Amberlite® IRN77 in acid form, marketed by Rohm and Haas) to remove the impurities. 33.2 ml of hydrazine hydrate are added to a solution of the diamide thus obtained in 1.4 l of water and the mixture is maintained at 80° C. for 3 hours. The mixture is acidified, at room temperature, by addition of 53 ml of aqueous 10N hydrochloric acid solution and the precipitate is separated out.

The residual solution is passed through a column of anion-exchange resin packed with 1 liter of basic Amberlite® IRA67 and then through a column of 150 ml of Amberlite® IRC50 in acid form and then grafted onto 4 liters of Amberlite® 200C, from which the product is eluted with aqueous $NH_4OH$ solution. The eluent is concentrated under reduced pressure to give the desired product in a yield of 70%.

HPLC chromatography: LiCrosphere® C 18 column; 5 µm (Merck); l=25 cm; d=4 mm.

Eluent(*): $CH_3CN$/P.I.C.® B8,0.05M (Waters) 5/95; flow rate: 1 ml/minute.

Retention time of the isomers: about 8 minutes. (*) P.I.C. B8: octanesulphonic acid/methanol/calcium acetate/water mixture.

B) Preparation of compound $C_2$ having formula IV in which

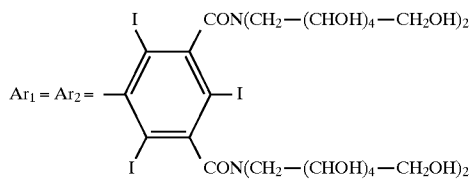

$T_1$—$Q_1$—$V_1$=$T_2$—$Q_2$—$V_2$=CONH—$CH_2$—CONH
Z=$H_2$N—$CH_2$—CONH

A solution of 59 g of the acid dichloride prepared in step (a) A, 200 g of the primary amine $C_1$ obtained in A and 29.5 ml of tributylamine in 400 ml of N-methylpyrrolidone or dimethylacetamide is maintained at 70° C. for 24 hours. The solvent is removed under reduced pressure and the residue is chromatographed on 3 kg of RP2 silanized silica marketed by Merck (DE), eluting with water, or through 4 kg of adsorbent XAD 1600 (Rohm and Haas), eluting with a $CH_3OH$/$H_2O$ mixture.

The product, obtained in a yield of 50%, is treated with hydrazine hydrate, as described above, to give the desired compound in a yield of 45%.

The elution volume of this compound during filtration through a Superdex® 30 gel in a 16 mm×60 cm column, marketed by Pharmacia, in a pH=7.2 buffer comprising 0.1M NaCl, 0.05M $NaH_2PO_4$ and 0.01M $NaN_3$, with a flow rate of 1 ml/minute, is 102 ml for an injected sample of 1 mg in 250 µl of buffer.

HPLC chromatography: Symmetry® C18 column; 5 µm (Merck); l=25 cm; d=4.6 mm.

Eluent: $CH_3CN$/0.01M $KH_2PO_4$ (15/85) (without $CH_3CN$ for the first 5 minutes)

Flow rate: 1 ml/minute

Retention time of the isomers: about 18 minutes.

C) Preparation of compound $C_3$ having formula IV with
$T_1$—$Q_1$—$V_1$=$T_2$—$Q_2$—$V_2$=CONH—$CH_2$—CONH
Z=$H_2$N—$CH_2$—CONH

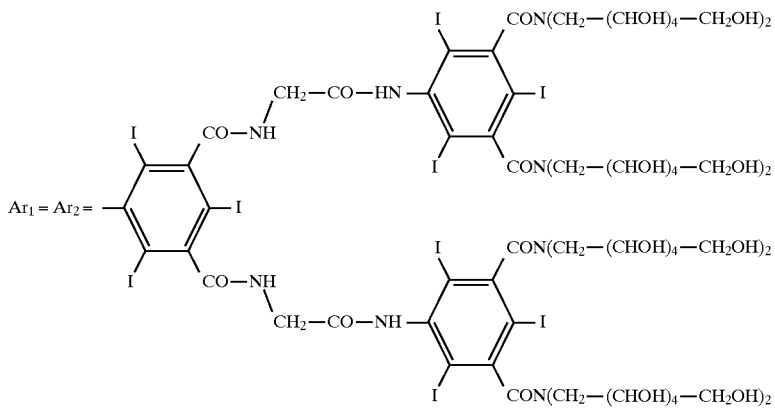

5.65 g of the acid dichloride of step (a) A, 48 g of the primary amine $C_2$ obtained in B and 3 ml of tributylamine in 100 ml of N-methylpyrrolidone or dimethylacetamide are maintained at 70° C. for 24 hours. After purification as in B, the compound containing the 7 iodophenyl rings is treated with hydrazine hydrate to give the crude primary amine. This is purified by passing it through ion-exchange resins in acidic and basic form as in preparation B. Optionally, a dia-ultrafiltration may then be carried out with a nova-type Minisette® cassette marketed by Filtron Technology Corp. (U.S.A.) with a polyether sulphone membrane having a cutoff threshold of 10 kdalton which allows the desired product to pass through. Yield: 65%.

The gel elution volume of this product under the same operating conditions as in preparation B is 91 ml, whereas it is 111 ml on a Superdex® 75 column.

HPLC chromatography: Symmetry® C18 column; 5 μm(Waters);

Eluent: $CH_3CN/0.01M\ KH_2PO_4$ (15/85) (without $CH_3CN$ for 5 minutes)

flow rate: 1 ml/minute

Retention time of the isomers: about 23 minutes.

Compounds $C_2$ and $C_3$ are substantially insoluble in acetone, acetonitrile, tetrahydrofuran or ethylene glycol mono- and dimethyl ethers; they are soluble in amides such as dimethylacetamide, dimethylformamide or N-methylpyrrolidone.

D) Preparation of compound $C_4$ having formula

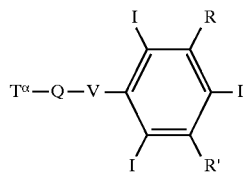

with R=COOH

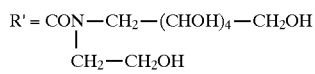

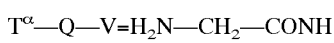

(1) 239 g of the acid dichloride described in preparation (a) A, 83 g of

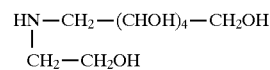

marketed by Aldrich, and 39 ml of triethylamine are dissolved in 1 liter of N,N-dimethylacetamide. After 24 hours at room temperature, 300 ml of water are introduced into the medium which is then maintained at 45° C. for 48 hours to hydrolyse the residual acid chloride. The solvents are then removed by distillation under reduced pressure and the residue is purified as above by passing it through a column of 500 ml of Amberlite® IRN77 and one of 3 kg of silanized RP2 silica.

The monoamide is thus obtained in a yield of 40%.

(2) This compound is treated with hydrazine hydrate and purified by passing it through acidic and basic ion-exchange resins as in preparation A. Yield: 70%.

E) Preparation of compound $C_5$ having formula IV with $T_1-Q_1-V_1=T_2-Q_2-V_2=CONH-CH_2-CONH$
$Z=H_2N-CH_2-CONH$

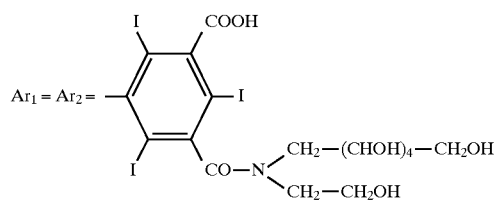

With operating conditions similar to those used in preparation B, the desired compound is obtained in a yield of 30%.

Its elution volume on filtration through Superdex® 30 gel under the above conditions is 92 ml.

The compounds given as examples are characterized by their retention times in steric exclusion chromatography (SEC) on 4 columns, mounted in series, marketed by Shodex (JP) under the references OH paK SB-800 HQ of diameter 8 mm and length 30 cm, packed with polyhydroxymethacrylate gel: SB-804 (exclusion limit=$10^6$ kdalton; standard: pullulan)+SB-803 ($10^5$)+SB-802-5 ($10^4$)+SB-802-5; the eluent is a mixture of aqueous 0.16M NaCl solution and acetonitrile (70/30—V/V)—flow rate 0.8 ml/minute—T= 30° C.

EXAMPLE 1

Compound No. 1 of formula I, in which $T_0$—$Q_0$—$V_0$=$T'_0$—$Q'_0$—$V'_0$=CONH—$CH_2$—CONH and

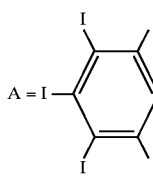 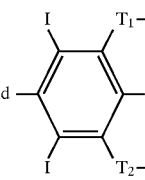 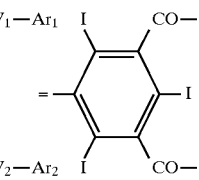 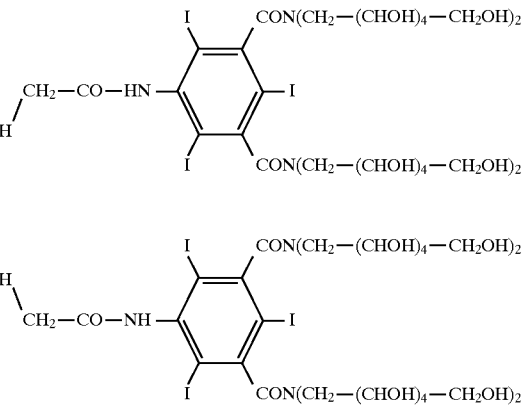

(1) Tetraiodoisophthalic acid:

30 ml of an aqueous solution of 2 g of NaNO, are introduced dropwise, at —5° C., into 60 ml of a solution of 11 g of 5-amino-2,4,6-triiodophenyl-1,3-dicarboxylic acid in aqueous 1N NaOH. The medium is then brought to pH 2 by addition of aqueous $H_2SO_4$ solution and is kept stirring for a further 3 hours at 5° C. before being brought to pH 5 by addition of aqueous 1N NaOH.

9.6 g of KI in solution in 20 ml of water are then added dropwise and the medium is then brought slowly to 45° C. and maintained at this temperature for 2 hours before being poured onto an ice/HCl mixture.

The precipitate formed is washed with aqueous sodium bisulphite solution and then with 150 ml of $CH_2Cl_2$. 11 g of beige-coloured crystals are isolated.

TLC: Merck silica plate. Rf=0.7 (Eluent $HCO_2H$/$CH_3COC_2H_5$/$C_6H_5CH_3$ 25/25/6).

(2) Tetraiodoisophthalic acid dichloride:

A mixture of 10.4 g of the above diacid and 150 ml of $SOCl_2$, with 0.2 ml of dimethylformamide, is maintained at its reflux temperature for 8 hours and the medium is then brought to dryness by evaporation under reduced pressure. The residue is crystallized from petroleum ether. 11 g of beige-coloured crystals are isolated.

TLC: Rf=0.1 (above conditions)

(3) Compound No. 1

16 g of compound $C_2$ obtained in preparation B, 4 g of tetraiodoisophthalic acid dichloride and 1.5 ml of triethylamine are introduced into 120 ml of dimethylformamide and the reaction medium is maintained at 80° C. for 12 hours. The precipitate is removed by filtration after cooling and the solvent is evaporated off under reduced pressure.

The residue, dissolved in 1 liter of water, is subjected to dia-ultrafiltration with a Minisette® cassette, with a membrane having a cutoff threshold of 5 kdalton, to give the desired product.

EXAMPLE 2

Compound having formula I, in which

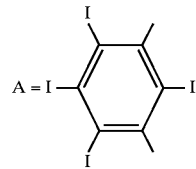

$T_0$—$Q_0$—$V_0$=$T'_0$—$Q'_0$—$V'_0$=CONH—$CH_2$—CONH and $T_1$—$Q_1$—$V_1$—$Ar_1$=$T_2$—$Q_2$—$V_2$—$Ar_2$=CONH—$CH_2$—CONH—Ar with Ar = 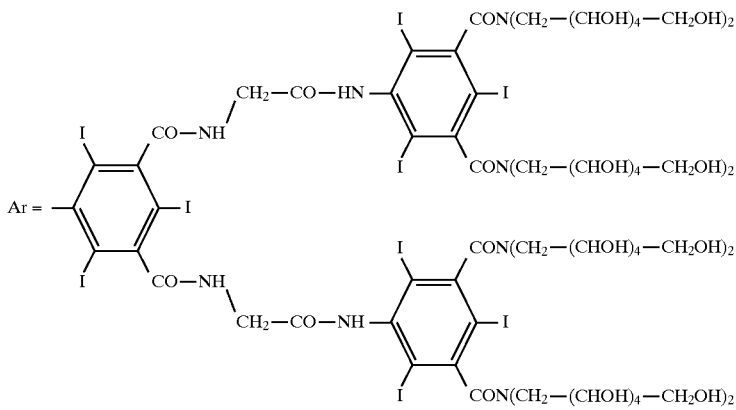

One equivalent of tetraiodoisophthalic acid dichloride prepared as in Example 1(2) and 2.4 equivalents of the amine $C_3$ obtained in preparation C, with one equivalent of tributylamine, are dissolved in the minimum amount of dimethylacetamide and the mixture is maintained at 80° C. for 10 hours before being treated as in Example 1.

The desired product is isolated after ultrafiltration of its aqueous solution in the same type of cassette as in Example 1, but containing a membrane whose cutoff threshold is 10 kdalton.

EXAMPLE 3

Compound No. 3 of formula I, in which
$T_0—Q_0—V_0=T'_0—Q'_0—V'_0=CONH—CH_2—CONH$
and A = 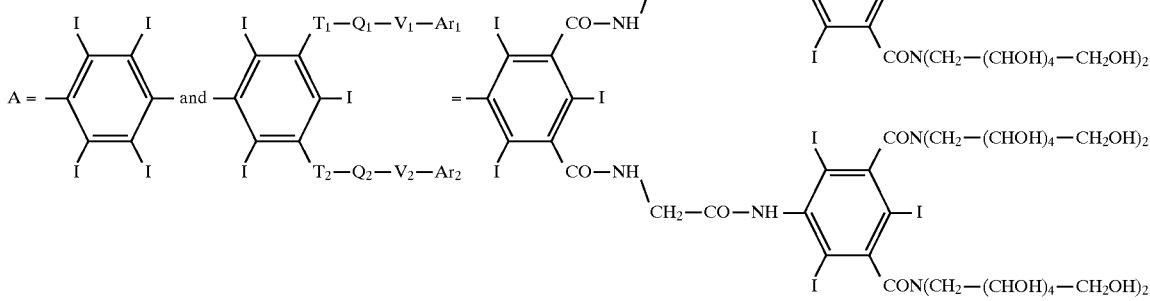

(1) Tetraiodoterephthalic acid 10 g of terephthalic acid are dissolved in 80 g of oleum containing 60% sulphur trioxide at 100° C. After 1 hour at this temperature, 40 g of iodine are added portionwise and the temperature is then raised to 180° C. and is maintained there for about 5 hours, after which the cooled medium is poured into 3 volumes of ice-water. The precipitate formed is dissolved in aqueous NaOH solution and the residual solid, essentially consisting of hexaiodobenzene, is isolated. The diacid is reprecipitated by acidification of the filtrate and is purified by treatment with boiling methanol.

Beige-coloured crystals. Yield 30%.

(2) Tetraiodoterephthalic acid dichloride 10 g of the diacid, 1.3 ml of dimethylformamide and 170 ml of $SOCl_2$ are maintained at the reflux temperature for 15 hours. After concentration under reduced pressure, petroleum ether is introduced onto the residue to crystallize it.

10 g of solid are thus isolated.

TLC: Rf=0.88 (conditions of Example 1-1).

(3) Compound No. 3

16 g of compound $C_2$ obtained in preparation B, 4 g of tetraiodoterephthalic acid dichloride and 1.5 ml of triethylamine are introduced into 120 ml of dimethylformamide and the reaction medium is maintained at 80° C. for 12 hours. The precipitate is removed by filtration after cooling and the solvent is evaporated off under reduced pressure. The residue, dissolved in 1 liter of water, is subjected to dia-ultrafiltration with a Minisette® cassette, with a membrane having a cutoff threshold of 5 kdalton, to give the desired product.

SEC: retention time of compound No. 3: 37.3 minutes and of the starting compound $C_2$: 38.7 minutes (SEC: Steric Exclusion Chromatography)

EXAMPLE 4

Compound No. 4 of formula I, in which

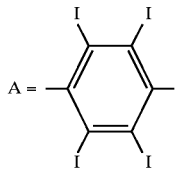

$T_0$—$Q_0$—$V_0$=$T'_0$—$Q'_0$—$V'_0$=CONH—$CH_2$—CONH and

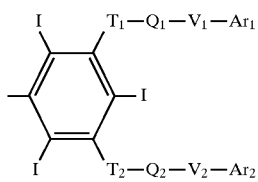

Given the low reactivity of the carboxylic acid substituted on the phenyl rings between two iodine atoms, this compound may be prepared by applying the same procedure as in Example 1.

EXAMPLE 5

Compound No. 5 of formula I, in which

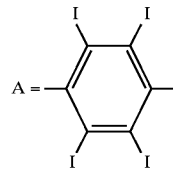

$T_0$—$Q_0$—$V_0$=$T'_0$—$Q'_0$—$V'_0$=CONH—$CH_2$—CONH and

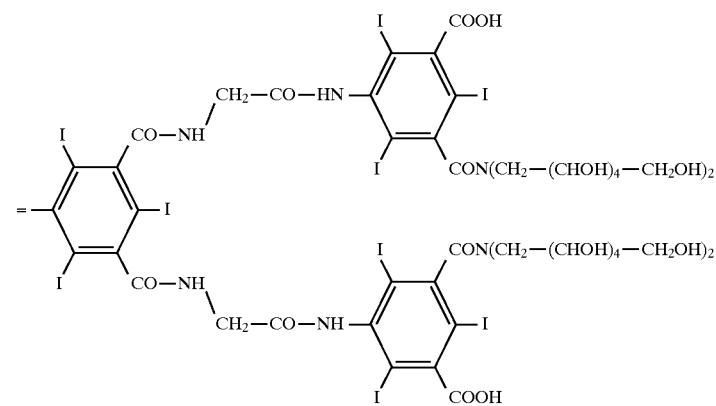

$T_1$—$Q_1$—$V_1$—$Ar_1$=$T_2$—$Q_2$—$V_2$—$Ar_2$=CONH—$CH_2$—CONH—Ar

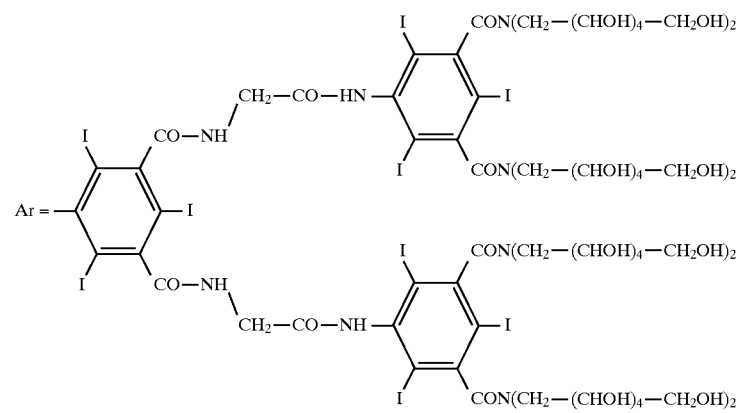

The procedure of Example 2 is applied to prepare compound No. 5 starting with compound $C_3$. Its prior dissolution in dimethylacetamide is advantageously carried out at 60° C. The final product is isolated in a yield of 50%.

EXAMPLE 6

Compound No. 6 of formula I, in which

A=—$CH_2$—; $T_0$—$Q_0$—$V_0$=$T'_0$—$Q'_0$—$V'_0$=CONH—$CH_2$—CONH and $T_1$—$Q_1$—$V_1$—$Ar_1$=$T_2$—$Q_2$—$V_2$—$Ar_2$=CONH—$CH_2$—CONH—Ar

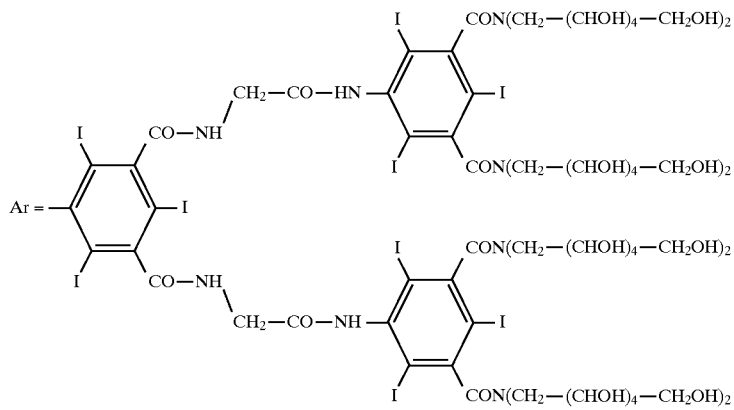

5.5 g of the amine $C_3$ are introduced very slowly with stirring, at about 60° C., into 20 ml of dimethylacetamide until completely dissolved, followed by 0.03 g of diacid, 0.11 g of 1-hydroxybenzotriazole, 0.16 g of 1-(3-dimethylaminopropyl)-3-ethylcarbodiimide hydrochloride and 0.13 ml of triethylamine. After stirring for 24 hours, 5 volumes of water are added and dia-ultrafiltration is carried out with a membrane having a cutoff threshold of 3 kdalton. The retentate is concentrated under reduced pressure to give 1 g of white powder.

SEC: retention time of compound No. 6: 34.4 minutes

EXAMPLE 7

Compound No. 7 of formula I, in which $A=-(CH_2)_4-$; $T_0-Q_0-V_0=T'_0-Q'_0-V'_0=CONH-CH_2-CONH$ and $T_1-Q_1-V_1-Ar_1=T_2-Q_2-V_2-Ar_2=CONH-CH_2-CONH-Ar$ The compound is prepared in a yield of 55% by applying the procedure described in Example 6, using a membrane with a cutoff threshold of 3 kdalton for the ultrafiltration.

SEC: retention time: 34.4 minutes.

EXAMPLE 8

Compound No. 8 of formula I, in which

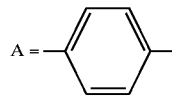

$T_0-Q_0-V_0=T'_0-Q'_0-V'_0=CONH-CH_2-CONH$ and $T_1-Q_1-V_1-Ar_1=T_2-Q_2-V_2-Ar_2=CONH-CH_2-CONH-Ar$

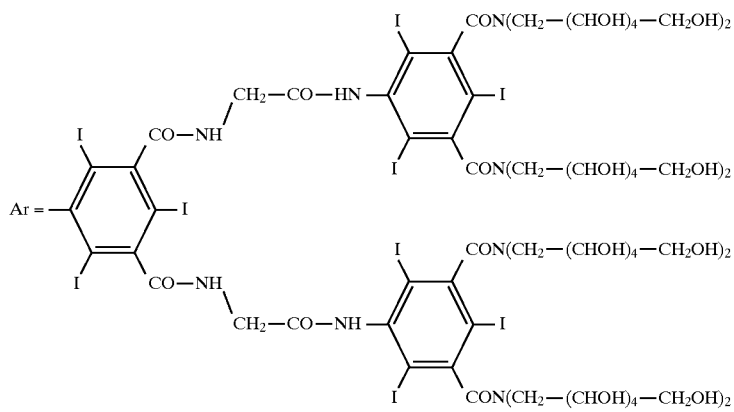

Ar = 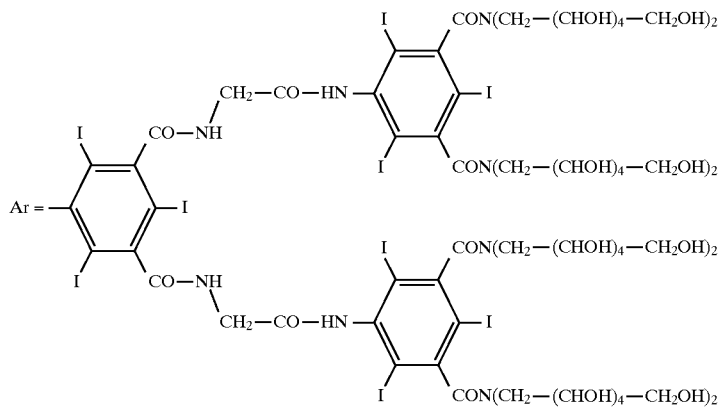

The compound is prepared in a yield of 50% by applying the procedure described in Example 6, using a membrane with a cutoff threshold of 3 kdalton for the ultrafiltration.

SEC: retention time: 34.3 minutes.

EXAMPLE 9

Compound No. 9 of formula I, in which $A = -CH_2 -$; $T_0 - Q_0 - V_0 = T'_0 - Q'_0 - V'_0 = CONH - CH_2 - CONH$ and

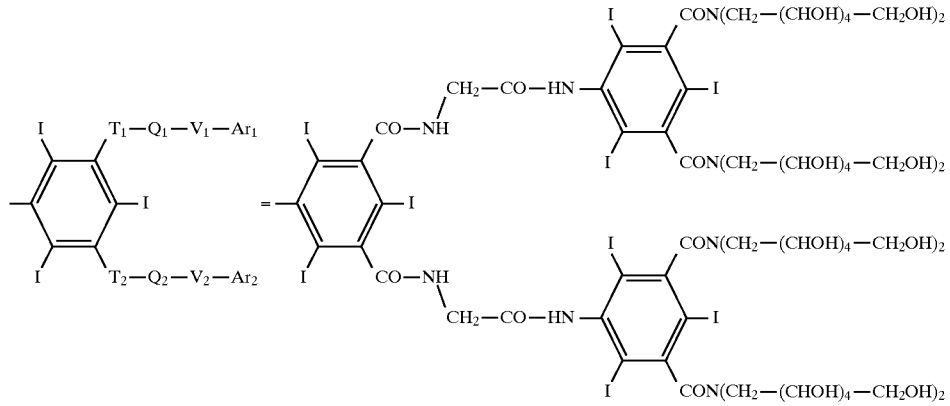

This compound is prepared in a yield of 48% by applying the procedure described in Example 6, but with the amine $C_2$ dissolved at about 20° C. and after ultrafiltration with a membrane having a cutoff threshold of 1 kdalton.

SEC: retention time of compound No. 9: 36.3 minutes, and of the starting compound $C_2$: 38.7 minutes.

EXAMPLE 10

Compound No. 10 of formula I, in which $A = -(CH_2)_4 -$; $T_0 - Q_0 - V_0 = T'_0 - Q'_0 - V'_0 = CONH - CH_2 - CONH$ and

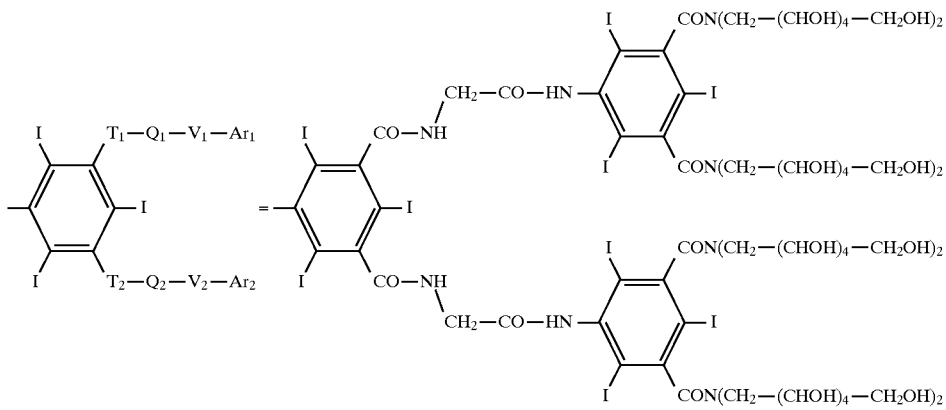

The compound is prepared in a yield of 52% by applying the procedure described in Example 9, using a membrane with a cutoff threshold of 1 kdalton for the ultrafiltration.

SEC: retention time: 36.2 minutes.

EXAMPLE 11

Compound No. 11 of formula I, in which

A = 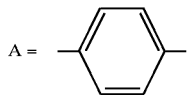

$T_0$—$Q_0$—$V_0$=$T'_0$—$Q'_0$—$V'_0$=CONH—$CH_2$—CONH and

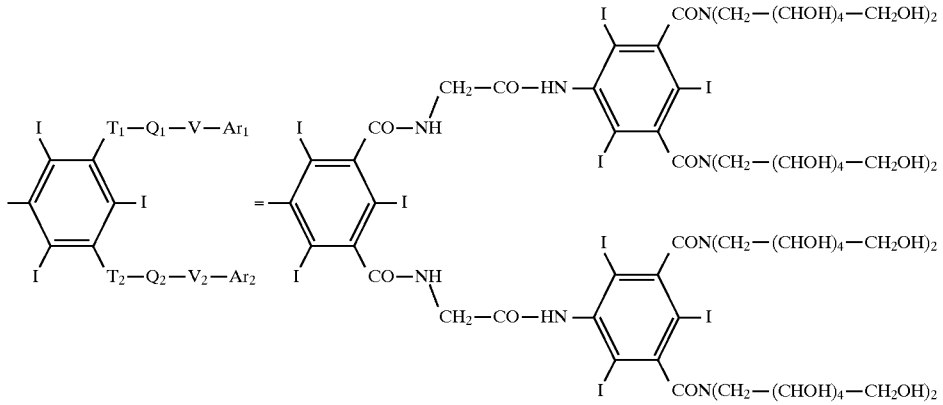

The compound is prepared in a yield of 48% by applying the procedure described in Example 9, using a membrane with a cutoff threshold of 1 kdalton for the ultrafiltration.

SEC: retention time: 36.3 minutes.

We claim:
1. Compound of formula

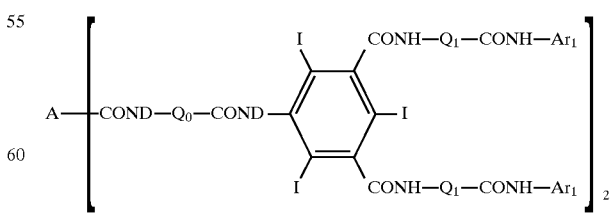

in which
D is selected from the group consisting of H, $C_1$ to $C_6$ alkyl and $C_1$ to $C_6$ hydroxyalkyl or polyhydroxyalkyl,
$Ar_1$ represents a group of formula (II):

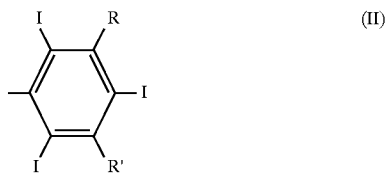 (II)

wherein R is COOH and R' is selected from the group consisting of $CONR'_1R'_2$ and $N(R'_1)COR'_2$, $R'_1$ and $R'_2$ being selected from the group consisting of H, $C_1$ to $C_4$ alkyl and $C_1$ to $C_8$ hydroxyalkyl or polyhydroxyalkyl such that $NR'_1R'_2$ comprises more than 4 hydroxyls, or R and R' are identical and represent —$CONR'_1R'_2$, $R'_1$ and $R'_2$ being selected from the group consisting of H, $C_1$ to $C_4$ alkyl and $C_1$ to $C_8$ hydroxyalkyl or polyhydroxyalkyl such that $R'_1$ and $R'_2$ together comprise more than 6 hydroxyls, or $Ar_1$ represents a group of formula (III):

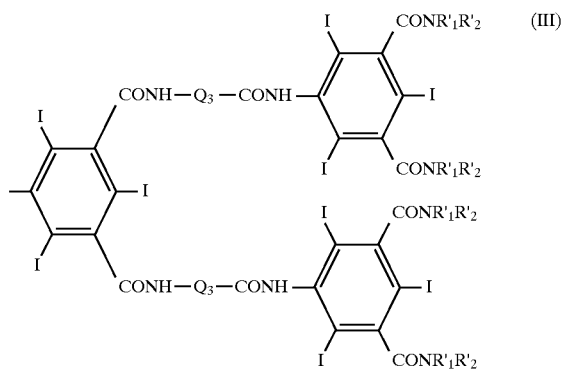 (III)

wherein $R'_1$ and $R'_2$ are selected from the group consisting of H, $C_1$ to $C_4$ alkyl and $C_1$ to $C_8$ hydroxyalkyl or polyhydroxyalkyl such that $R'_1$ and $R'_2$ together comprise more than 6 hydroxyls, $Q_0$, $Q_1$ and $Q_3$, which are identical or different, are selected from the group consisting of $C_1$ to $C_6$ alkylene and $C_1$ to $C_6$ hydroxyalkylene or polyhydroxyalkylene, A is a biocompatible radical from an aliphatic or aromatic molecule of molecular weight less than 1200 having two free valences for linking to COND, as well as their pharmaceutically acceptable salts with bases.

2. Compound according to claim 1, wherein $Ar_1$ is formula (II), R is COOH and R' is $CONR'_1R'_2$, $R'_1$ and $R'_2$ comprising together more than 6 hydroxyls.

3. Compound according to claim 1, wherein $Ar_1$ is formula (II), R and R' are identical and represent $CONR'_1R'_2$, $R'_1$ and $R'_2$ comprising together more than 8 hydroxyls.

4. Compound according to claim 1, wherein $Ar_1$ is formula (III) and $R'_1$ and $R'_2$ comprise more than 8 hydroxyls.

5. Compound according to claim 1, wherein $Q_0$, $Q_1$ and $Q_3$ are $CH_2$ and D is H.

6. Compound according to claim 3, wherein $Q_0$ and $Q_1$ are $CH_2$ and D is H.

7. Compound according to claim 4, wherein $Q_0$, $Q_1$ and $Q_3$ are $CH_2$ and D is H.

8. Compound according to claim 1, wherein A is an aliphatic group, $Q_0$, $Q_1$ and $Q_3$ are $CH_2$, D is H and R and R' are $CONR'_1R'_2$ when $Ar_1$ is formula (II).

9. Compound according to claim 1, wherein A is a phenyl ring, optionally substituted, $Q_0$, $Q_1$ and $Q_3$ are $CH_2$, D is H and R and R' are $CONR'_1R'_2$ when $Ar_1$ is formula (II).

10. Compound according to claim 9, wherein $R'_1$ and $R'_2$ comprise together more than 8 hydroxyls.

11. Compound according to claim 1, wherein
A is

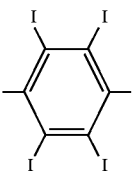

$Ar_1$ is formula (II), $Q_0$ and $Q_1$ are $CH_2$, D is H, R and R' are $CONR'_1R'_2$, $R'_1$ and $R'_2$ being $C_1$–$C_8$ hydroxyalkyl or polyhydroxyalkyl.

12. Compound according to claim 11, wherein $R'_1$ and $R'_2$ comprise together more than 8 hydroxyls.

13. Compound according to claim 1, wherein
A is
hydroxyalkyl or polyhydroxyalkyl.

14. Compound according to claim 13, wherein $R'_1$ and $R'_2$ comprise together more than 8 hydroxyls.

15. Contrast agent composition for X-ray medical imaging, comprising as active ingredient a compound according to claim 1.

16. Contrast agent composition for X-ray medical imaging, comprising as active ingredient a compound according to claim 11.

17. Contrast agent composition for X-ray medical imaging, comprising as active ingredient a compound according to claim 12.

18. Contrast agent composition for X-ray medical imaging, comprising as active ingredient a compound according to claim 13.

19. Contrast agent composition for X-ray medical imaging, comprising as active ingredient a compound according to claim 14.

20. A method for enhancing X-ray image comprising administration to a patient of a compound according to claim 1.

21. A method for enhancing X-ray image comprising administration to a patient of a compound according to claim 11.

22. A method for enhancing X-ray image comprising administration to a patient of a compound according to claim 12.

23. A method for enhancing X-ray image comprising administration to a patient of a compound according to claim 13.

24. A method for enhancing X-ray image comprising administration to a patient of a compound according to claim 14.

* * * * *